US007927603B2

(12) United States Patent
Kerner et al.

(10) Patent No.: US 7,927,603 B2
(45) Date of Patent: Apr. 19, 2011

(54) RECOMBINANT FUSION-ENZYME WITH REPAIR ACTIVITY ON DNA LESIONS PRODUCED BY UV RADIATION; ITS USAGE, PREPARATION AND PURIFICATION METHOD; A METHOD TO STABILIZE ENZYMES AND TREATMENT METHODS

(76) Inventors: Nestor Alberto Kerner, Buenos Aires (AR); Guillermo Basílico, Buenos Aires (AR); Mauricio Seigelchifer, Buenos Aires (AR)

( * ) Notice: Subject to any disclaimer, the term of this patent is extended or adjusted under 35 U.S.C. 154(b) by 631 days.

(21) Appl. No.: 11/750,096

(22) Filed: May 17, 2007

(65) Prior Publication Data

US 2007/0280923 A1    Dec. 6, 2007

(30) Foreign Application Priority Data

May 31, 2006    (AR) .............................. P060102256

(51) Int. Cl.
*A61K 39/00* (2006.01)
*A61K 38/43* (2006.01)
(52) U.S. Cl. .................... 424/192.1; 424/94.1; 536/23.1
(58) Field of Classification Search .............. 424/94.6, 424/192.1, 94.1; 536/23.1
See application file for complete search history.

(56) References Cited

OTHER PUBLICATIONS

PNAS; Feb. 29, 2000; vol. 97; No. 5; pp. 2150-2156; Steffen Emmert et al.;The Xeroderma Pigmentosum Group C Gene Leads to Selective Repair of Cyclobutane Pyrimidine . . . .
Clinical Cancer Research; vol. 8, pp. 2985-2991; Sep. 2002; Lili Liu et al.; Base Excision Repair as a Therapeutic Target in Colon Cancer.
Mutation Research 460 (2000) 257-275; Kosuke Morikawa et al.; pp. 258-270; Three-Dimensional Structural View of Damaged-DNA Recognition; T4 Endonuclease V, . . . .
Journal of Dermatological Science; Guillermo Basilico et al.; pp. 82-88; UV-Specific DNA Repair Recombinant Fusion Enzyme: A New Stable Pharmacologically Active . . . , (2005) 39, 81-88.
The Lancet; vol. 357, No. 9290; pp. 926-929; Daniel Yarosh et al.; Effect of Tpically Applied T4 Endonuclease V in Liposomes on Skin Cancer in Xeroderma Pigmentosum: a . . . , (2001).
National Academy of Sciences USA, vol. 94, pp. 593-598, Jan. 1997 Genetics; Susumu Shiota et al.; UV Endonuclease of *Micrococcus luteus*, a Cyclobutane Pyrimidine Dimer . . . .
Annual Review Biochemistry, 1996, 65:135-67; pp. 136-167; Richard D. Wood; DNA Repair in Eukaryotes.
Methods in Enzymotology, vol. 65; pp. 185-201; Sheikh Riazuddin; Purification and Properties of Phrimidine Dimer Specific Endonucleases from *Micrococcus luteus* (1977).
Protein Expression and Purification 22, 399-405 (2001); pp. 399-405; Ral Paul et al.; Overexpression and Purification of *Helicobacter pylori* Flavodoxin and Induction . . . .
Protein Expresson and Purification, 23 22-32 (2001); pp. 22-32; Yves Nomine et al.; Formation of Soluble Inclusion Bodies by HPV E6 Oncoprotein Fused to Maltose-Binding . . . .
Biochimica et Biophysica Acta, 698 (1982) 287-294; pp. 287-295; N. V. Tomilin et al. An Analysis of the Repair Processes in Ultraviolet Irradiated *Micrococcus luteus* Using . . . .
Base Excision Repair of DNA Damage, edited by Ian D. Hickson; 1997 Landes Bioscience; pp. 31-44; Serge Boiteux et al.; Repair of Oxidized Purines in DNA.

*Primary Examiner* — Tekchand Saidha
(74) *Attorney, Agent, or Firm* — Lackenbach Siegel, LLP

(57) ABSTRACT

A recombinant fusion enzyme repairs DNA damaged by UV radiation, and the method of preparing recombinant fusion enzyme. The method includes the fusion of an enzyme coded by a gene isolated from *Micrococcus luteus* and a stabilizing peptide having the amino acid sequence described in SEQ ID NO 2. A treatment method intended to repair DNA lesions produced in cells exposed to UV radiation and to repair cell anomalies or lesions produced by sun exposure. Such treatment consists of the administration of a effective amount of recombinant fusion enzyme, or a vector containing the gene coding to the recombinant fusion enzyme, to patients requiring such treatment.

9 Claims, 16 Drawing Sheets

FIGURE 1

SEQ ID N° 1

Nucleotide sequences of genes coding to recombinant fusion enzyme *(RFE)*

5'ATG TGT GAT TTA CCT CAA ACT CAT TCT CTT GGT TCT CGT CGT ACT CTG ATG CTG CTG GCA CAG ATG CGT CGT ATT TCC CTG TTC AGC TGC CTG AAA GAC CGT CAC GAC TTC GGC TTT CCG CAA GAA GAG TTC GGC AAC CAA TTC CAG AAA GCT GAA ACT ATC CCA GTA CTG CAC GAA ATG ATC CAA CAG ATC TTG ATG CGC CTG TGG ACC CTT CAC CCC CGC CAC CTC GAC CGC CAG GGC CTG ACG GGC GCC TGG CGC GAG GCC CTG CTC GCG CAG GCC GTC CTG GCC GGC CGC ACG CGC GGG TAT CGG GAC CAC CCG CAG CTG CTG AGG TTC CGG GAG CAC CCG GAC CCG TCC GGC GCG ATC GGT GCG TTC CTC TCC GGC CTC GAG GCC GAG GCC ACG GCG CGC GGC TAT CGC TTC GAC CAC TCC CGG ATC GAC CGG CCG TGC CCC GCC CCC GAC GGC GCC GTG CGC ATC CCG CCG GCC GGT CTC GCG CCG ATC CCG GCC ACC ACG GGC CAG CGC GAC CTG GAG TGG CGT CAC CTG TGC GCC AAG CTG GCC GTG CGC AGC CCC GCC TGG CTC GAA CAG TGG TCG GAC ACG CCC GTC CCC GAC GTG CAC CCG CTG TTC ACG ATC GTC CCT GGG CCG GTC GCC TCC TGG GAG CGC GCC TGA 3'

FIGURE 2

SEQ. ID NO. 4

Aminoacid sequences of recombinant fusion enzyme *(RFE)*

Met Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile Leu Met Arg Leu Trp Thr Leu His Pro Arg His Leu Asp Arg Gln Gly Leu Thr Gly Ala Trp Arg Glu Ala Leu Leu Ala Gln Ala Val Leu Ala Gly Arg Thr Arg Gly Tyr Arg Asp His Pro Gln Leu Leu Arg Phe Arg Glu His Pro Asp Pro Ser Gly Ala Ile Gly Ala Phe Leu Ser Gly Leu Glu Ala Glu Ala Thr Ala Arg Gly Tyr Arg Phe Asp His Ser Arg Ile Asp Arg Pro Cys Pro Ala Pro Asp Gly Ala Val Arg Ile Pro Pro Ala Gly Leu Ala Pro Ile Pro Ala Thr Thr Gly Gln Arg Asp Leu Glu Trp Arg His Leu Cys Ala Lys Leu Ala Val Arg Ser Pro Ala Trp Leu Glu Gln Trp Ser Asp Thr Pro Val Pro Asp Val His Pro Leu Phe Thr Ile Val Pro Gly Pro Val Ala Ser Trp Glu Arg Ala

FIGURE 3

SEQ. ID NO. 2

ATG TGT GAT TTA CCT CAA ACT CAT TCT CTT GGT TCT CGT CGT ACT CTG ATG
CTG CTG GCA CAG ATG CGT CGT ATT TCC CTG TTC AGC TGC CTG AAA GAC
CGT CAC GAC TTC GGC TTT CCG CAA GAA GAG TTC GGC AAC CAA TTC CAG
AAA GCT GAA ACT ATC CCA GTA CTG CAC GAA ATG ATC CAA CAG ATC TT

FIGURE 4

SEQ. ID NO. 3

Aminoacid Sequence correponding to stabilizing peptide.

*Met Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile Leu*

**Typical aspect of the yellow colonies of *Micrococcus luteus***

Culture was grown in LB agar, at 30°C during 16 hours.

PCR amplification of the native UveA gene from *M. luteus*

Electrophoresis in 1.0% agarose gel. PCR amplification for the whole UveA gene from *M. luteus*, using oligonucleotides MLN and MLC. Lanes 1 and 4: φx174/*Hae*III molecular marker. Lanes 2 and 3: PCR amplification product.

FIGURE 7

Fifteen percent SDS-PAGE. Electrophoresis of crude extract preparations from *E. coli* ENV1 transformed with pEX-(RFE), showing the expression of the recombinant fusion enzyme.

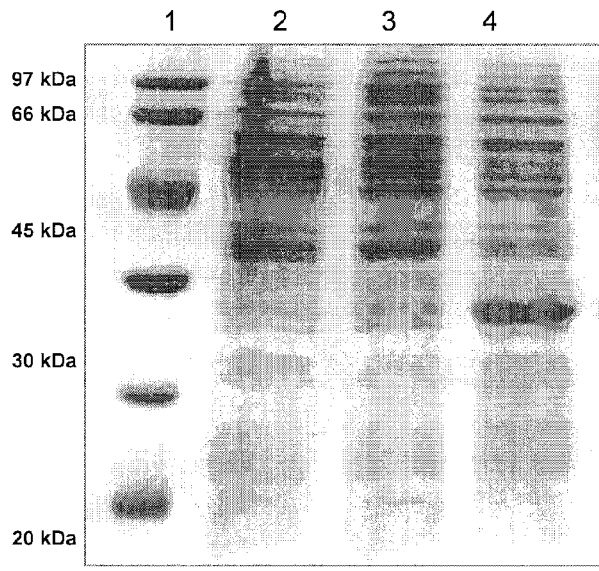

Lane 1: molecular weight marker

Lane 2: inoculum from ENV1 (*pEX- (RFE)*) culture;

Lane 3: ENV1 (*pEX- (RFE)*) culture without induction;

Lane 4: ENV1 (*pEX- (RFE)*) culture induced at 42°C.

Each lane was loaded with a crude extract preparation corresponding to aproximatelly 1,0 x $10^9$ bacteria.

**Fifteen percent SDS-PAGE. Expression of recombinant fusion enzyme in fractions soluble and insoluble of ENV1 (*pEX- (RFE)*)**

Lane 1: ENV1 (*pEX- (EFR)*) culture, without induction;

Lane 2: ENV1 (*pEX- (EFR)*) culture, induced at 42°C;

Lane 3: soluble fraction from the induced culture;

Lane 4: insoluble fraction from induced culture;

Lane 5: molecular weight marker.

Western Blot Analysis. Expression of the recombinant fusion enzyme from an induced culture.

Lane 1: *IFNα* (50 ng).

Lane 2: bovine serum albumin (5,0 μg).

Lane 3: inoculum from ENV1 (*pEX- (EFR)*) culture.

Lane 4: ENV1 (*pEX- (EFR)*) culture, without induction.

Lane 5: ENV1 (*pEX- (EFR)*) culture, induced at 42°C.

Bacterial growth curve during the fermentation process

Fermentation samples were separated by 15% SDS-PAGE electrophoresis stained with Coomassie Blue.

Lanes 2 - 9: fermentation samples.
Lanes 1 and 10: molecular weight marker.

UV-specific endonuclease activity assays of recombinant fusion enzyme (RFE) preparations.

Lanes 1 and 6: 200 ng of *pUC19*, without irradiation;

Lanes 2, 3, 4, 5 and 7: 200 ng of irradiated *pUC19*.

Lanes 1 - 5: progressive amounts of *EFR* (from 50 to 400 ng)

Calles 6 - 7: negative control for the reaction, without enzymatic activity.

Analysis of the protein profile by 15% SDS-Page stained with Coomassie Blue

Lane 1: molecular weight marker.

Lane 2: Recombinant fusion enzyme standard, purified by HPLC.

Lane 3: Oxidized, dialyzed and clarified product from every solubilization. The inclusion bodies were solubilized with 8M urea.

FIGURE 14

Fifteen percent SDS-Page electrophoresis stained with Coomassie Blue. Analysis of protein profile for every purification step.

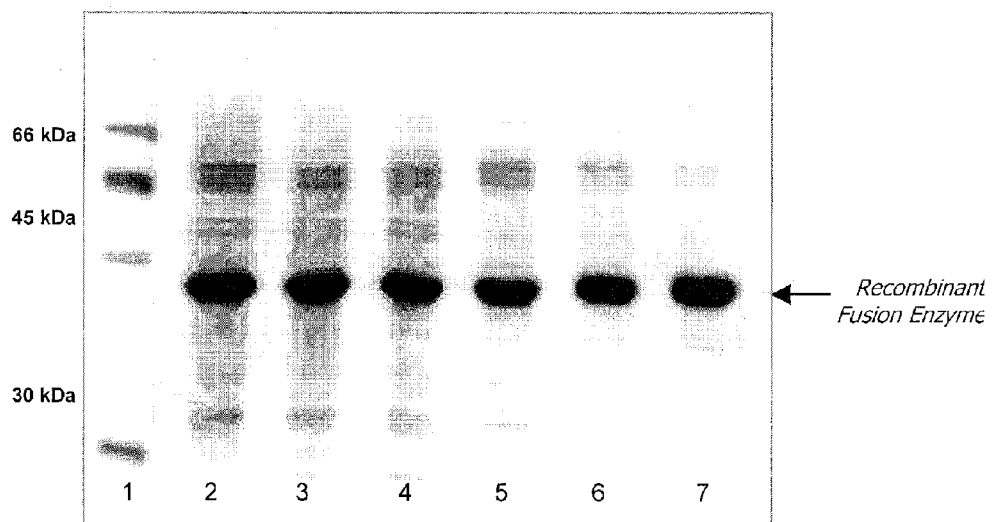

Calle 1: molecular weight marker

Calle 2: inclusion bodies at process' start up.

Calle 3: After First washing with Solution A.

Calle 4: After washing with Solution A + 2 M urea.

Calle 5: After washing with Solution B.

Calle 6: After Second washing with Solution A.

Calle 7: After Third washing with Solution A.

Densitometry of protein profile obtained from recombination fusion enzyme (RFE) preparation submitted to electrophoresis in a 15% SDS-Page stained with Coomassie Blue a: inclusion bodies present at the beggining of the purification process.
b: inclusion bodies after third washing with Solution A.

The main peak in both figures corresponds to RFE product.

Comparative stability between recombinant fusion enzyme (RFE) and native UveA

The *in vitro* repair activity from each preparation (stored under the indicated temperature) was measured and depicted above. The activity was referred to as percentage of activity relative to time zero.

SEQUENCE LISTING

```
<160> NUMBER OF SEQ ID NOS: 4

<210> SEQ ID NO 1
<211> LENGTH: 660
<212> TYPE: DNA
<213> ORGANISM: Homo sapiens
```

-continued

<400> SEQUENCE: 1

| | | | | | |
|---|---|---|---|---|---|
| atgtgtgatt | tacctcaaac | tcattctctt | ggttctcgtc | gtactctgat | gctgctggca | 60 |
| cagatgcgtc | gtatttccct | gttcagctgc | ctgaaagacc | gtcacgactt | cggctttccg | 120 |
| caagaagagt | tcggcaacca | attccagaaa | gctgaaacta | tcccagtact | gcacgaaatg | 180 |
| atccaacaga | tcttgatgcg | cctgtggacc | cttcacccc | gccacctcga | ccgccagggc | 240 |
| ctgacgggcg | cctggcgcga | ggccctgctc | gcgcaggccg | tcctggccgg | ccgcacgcgc | 300 |
| gggtatcggg | accacccgca | gctgctgagg | ttccgggagc | acccggaccc | gtccggcgcg | 360 |
| atcggtgcgt | tcctctccgg | cctcgaggcc | gaggccacgg | cgcgcggcta | tcgcttcgac | 420 |
| cactcccgga | tcgaccggcc | gtgccccgcc | cccgacggcg | ccgtgcgcat | cccgccggcc | 480 |
| ggtctcgcgc | cgatcccggc | caccacgggc | cagcgcgacc | tggagtggcg | tcacctgtgc | 540 |
| gccaagctgg | ccgtgcgcag | ccccgcctgg | ctcgaacagt | ggtcggacac | gcccgtcccc | 600 |
| gacgtgcacc | cgctgttcac | gatcgtccct | gggccggtcg | cctcctggga | gcgcgcctga | 660 |

<210> SEQ ID NO 2
<211> LENGTH: 194
<212> TYPE: DNA
<213> ORGANISM: Homo sapiens

<400> SEQUENCE: 2

| | | | | | |
|---|---|---|---|---|---|
| atgtgtgatt | tacctcaaac | tcattctctt | ggttctcgtc | gtactctgat | gctgctggca | 60 |
| cagatgcgtc | gtatttccct | gttcagctgc | ctgaaagacc | gtcacgactt | cggctttccg | 120 |
| caagaagagt | tcggcaacca | attccagaaa | gctgaaacta | tcccagtact | gcacgaaatg | 180 |
| atccaacaga | tctt | | | | | 194 |

<210> SEQ ID NO 3
<211> LENGTH: 103
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t

```
<400> SEQUENCE: 3
mtcysasrgn thrhssrgys rargargthr mtaagnmtar gargsrhsrc ysysasargh    60
sashgyhrgn gghgyasngn hgnysaagth rrvahsgmtg ngn                     103

<210> SEQ ID NO 4
<211> LENGTH: 369
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t

<400> SEQUENCE: 4
mtcysasrgn thrhssrgys rargargthr mtaagnmtar gargsrhsrc ysysasargh    60
sashgyhrgn gghgyasngn hgnysaagth rrvahsgmtg ngnmtargtr thrhsrargh   120
sasarggngy thrgyaatra rggaaaagna avaaagyarg thrarggyty rargashsrg   180
nargharggh srasrsrgya agyaahsrgy gaagaathra aarggytyra rghashssra   240
rgasargrcy sraarasgya avaargrraa gyaarraath rthrgygnar gasgtrargh   300
scysaaysaa vaargsrraa trggntrsra sthrrvaras vahsrhthrv argyrvaaas   360 rtrgargaa                                                          369
```

RECOMBINANT FUSION-ENZYME WITH REPAIR ACTIVITY ON DNA LESIONS PRODUCED BY UV RADIATION; ITS USAGE, PREPARATION AND PURIFICATION METHOD; A METHOD TO STABILIZE ENZYMES AND TREATMENT METHODS

PRIOR RELATED APPLICATION

This application claims priority to Argentine Patent Application No. P06 01 02.256, filed May 31, 2006.

FIELD OF INVENTION

The invention refers to DNA-repairing enzymes, particularly to the creation of a recombinant fusion-enzyme, obtained from the fusion of an enzyme expressed from a gene previously isolated from *Micrococcus luteus* and a stabilizing peptide, as well as its expression system in bacteria, its purification process and its pharmacological activity. This enzyme proved to be most stable and protective form for XPC cells (known to be sensitive to UV radiation as they are not genetically efficient in repairing DNA), when submitted to UV radiation.

STATE OF THE ART

Skin cancer is a serious human disease. Every year millions of people around the world develop basal and squamous cell carcinomas, the two most commonly found skin cancer types. The etiology is related to several factors including the type of skin, age, frequency and exposition index to sun rays, which is the main cause of genetic mutations on skin cells.

When the DNA is exposed to UV radiation, adjacent pyrimidines may become hot-spot sites for dimers of cyclobutane pyrimidine formation, as well as the 6-4 pyrimidine fotoproducts. These DNA lesions may constitute a source for new mutations that would contribute to photocarcinogenesis, in the case the involved genes are key for these processes, as the tumor suppressor genes "p53" and "ptch".

Mutations in these genes frequently occur in squamous and basal carcinomas, as well as in actinic keratosis.

*Xeroderma pigmentosum* is a human genetic disease which individuals develop pigmentation anomalies, lesions and malignancies on the skin exposed to the sun. As described by Fridberg et al in DNA Repair and Mutagenesis (ASM Press, 1995, pages 634-646) cells from individuals with *Xeroderma pigmentosum* are unable to repair structural damage to DNA, particularly those produced by UV light. These individuals preset a skin cancer incidence very much higher than the general United States population. Up to date there is no cure for this disease and treatment consists in avoiding sun exposure and removing skin lesions. Among these patients, death usually takes place 30 years earlier than in the rest of US general population.

Research on basic mechanisms of DNA-repair has allowed to identify the biochemical pathways involved on DNA-repair induced by UV light. Bacterial repair systems have demonstrated to be very different from human repair systems.

On the 60's, the T4 phage UV-specific endonuclease (named T4 endonuclease V) was described as the first UV specific glycosilase having a combined glycosilase and abasic endonuclease activity. This enzyme has been the enzymatic prototype model of the Base Excision Repair (BER) with double activity.

T4 endonuclease V recognizes the pyrimidines dimers and performs two different catalytic activities: it disrupts the glicosilic bound in the 5' end of the dimer and then it produces an incision of a phosphodiester bound on the 3' side of the abasic site (Friedberg et al., 1995).

Another example is given by the microorganism *Micrococcus luteus*, which has a UV specific endonuclease. The cloning and characterization of this enzyme, named UveA, has allowed to determine structural and functional characteristics shared with T4 endonuclease V (Shiota and Nakayama, 1997).

UveA is a small monomeric molecule of 18 KDa, having no cofactor requirements and catalyzing the double enzymatic reaction in a similar way as the T4 endonuclease.

These enzymes have been purified from microorganisms. The endonuclease V enzyme (also referred as T4 endonuclease V or denV endonuclease) is able to perform DNA-repair in human cells, as shown by the survival of cells submitted to increasing UV exposition after enzyme treatment.

However, up to date the clinical use of these exogenous enzymes in DN repair systems has been limited, since nobody has been able to obtain a stable enzyme with a high specific activity, expressed in an efficient and high-yield recombinant system allowing to purify industrial amounts of DNA-repair enzymes and that the enzyme be safe to administer to living human cells.

Therefore, there is still the need to produce a DNA-repair enzyme specific to UV damage, with prolonged stability, obtained from a low-cost and highly productive system and in a purified state. The subject of this invention, a recombinant fusion enzyme obtained from merging an enzyme (coded by the gen UveA of *M. luteus*) with a stabilizing peptide, has proven to be pharmacologically active in human cells (Guillermo Basilico, Carolina Alvarez Roger, Mauricio Seigelchifer and Nestor Kerner, UV-specific DNA repair recombinant fusion enzyme: a new stable pharmacologically active principle suitable for photoprotection. Journal of Dermatological Science, 39 (2), 81-88).

BRIEF DESCRIPTION OF THE DRAWINGS

FIG. 1: Nucleotide sequence of recombinant fusion enzyme gene (SEQ ID NO: 1)

FIG. 2: amino acid sequence of recombinant fusion enzyme (SEQ ID NO: 4)

FIG. 3: nucleotide sequence of stabilizing peptide (SEQ ID NO: 2)

FIG. 4: amino acid sequence of stabilizing peptide (SEQ NO: 3)

FIG. 7: Expression of the recombinant fusion enzyme in crude extract of transformed *E. coli* ENV1 culture with plasmid pEX-"recombinant fusion enzyme".

FIG. 14: Purification of soluble fraction from inclusion bodies. Analysis of intermediate purification steps. Samples were run on a 15% SDS-polyacrylamide gel electrophoresis and stained with Coomassie Blue.

DETAILED DESCRIPTION OF THE INVENTION

Figure 5:
FIG. 5: Typical morphology of yellow colonies of *Micrococcus luteus*.

Aiming to the development of a new pharmacologically active ingredient intended to treat and prevent DNA lesions by acting on the cellular repair system, we have worked on the construction of a recombinant fusion enzyme (SEQ ID NO 4). Surprisingly the invention's authors found that the characteristics of this recombinant fusion enzyme, together with the easy obtention processes, purification and stability, makes it an adequate molecule for the development of a technology to be applied in enzymatic therapy.

One major point of this invention is the fact that the expression system of this enzyme is able to produce very important amounts of recombinant product; and that this production level can still be increased if the process is optimized at industrial scales.

Additionally, the recombinant fusion enzyme has demonstrated to be very stable both at 4° C. as at room temperature, which facilitates its transportation and formulation.

Preliminary studies performed by our laboratory, as also shown by literature (Riazuddin, 1980), demonstrated the enzymatic instability of UveA from *M. luteus*. In order to obtain more stable forms, we have made several genetic engineering constructs, containing a stabilizing peptide on the amino end of the enzyme.

There are examples on literature where some peptides fused to the amino terminal of recombinant proteins can provide a better stability, as for example glutation-S-transferase, thioredoxin, some peptides formed by histidines and the maltose-union protein, among others (Paul et al., 2001; Nomené et al., 2001).

The peptide sequence chosen to make the fusion had to be basically easy to express in recombinant systems as well as pharmacologically safe as to toxicity risks. Different size and primary structures were then elected based on the absence of historical toxicity or pharmacological risk. Using this methodology and by genetic engineering a recombinant fusion enzyme named "recombinant fusion enzyme (SEQ ID NO 4)", coded by the nucleotide sequence SEQ ID NO 1 was obtained. Said enzyme was constructed by fusion of the enzyme coded by the gen UveA with a peptide chain 65-amino acid long (SEQ ID NO 3) coming from human interferon alpha 2 cDNA. This fusion protein, which maintains the enzymatic specificity for repairing UV lesions, has been used to comparatively measure the stability between this enzyme and the UveA purified from *M. luteus*.

The biologically active homologous for the nucleotide sequence SEQ ID NO 1, have also been included into the scope of this invention. Such homologous must retain the ability to repair the DNA from skin cells damaged by UV radiation. The biologically active homologous include, for example, the sequences of the invention with one or more substitution, suppression or nucleotide insertion.

The substantially homologous sequences to this invention includes variants of revealed sequences as those originated by site-directed mutagenesis as well the synthetically-derived sequences. two nucleotide sequences are considered to be substantially homologous when the sequence homology is at least approximately 70%, preferably at least approximately 80%, more preferably at least approximately 90%, even more preferably at least approximately 95%.

The results obtained from stability studies performed with the recombinant fusion enzyme and the native UveA enzyme purified from a *M. luteus* culture have indicated that the fusion protein is remarkably more stable, both at 4° C. and at room temperature.

This invention will be depicted in details.

1. Genomic DNA Extraction from *M. luteus*

The UveA gene was amplified from the genomic DNA of *M. luteus*. The lyophylized *M. luteus* strain (ATCC 9341) was resuspended in LB broth (casein peptone 10 g/l, yeast extract 5 g/l, NaCl 10 g/l), plated on LB agar (LB broth with agar 15 g/l) and incubated at 30° C. until colony growth (FIG. 5). New cultures were prepared from these colonies, incubating in LB broth at 30° C. and 250 rpm. The obtained liquid cultures were stored on cryotubes at −80° C., previous 20% glycerol addition.

2. Genomic DNA Extraction from *M. luteus*

Genomic DNA extraction was performed based on protocols available for Gram-negative organisms. A *M. luteus* overnight culture, grown as described previously, was harvested at 1,000×g during 10 minutes. The precipitated cells were briefly washed with physiological solution and centrifuged at 1,000×g during 10 min. The cells were resuspended in a 500 µl of lysis solution (20% sacarose, 25 mM Tris-HCl pH 7.4, 10 mM EDTA, 6 mg/ml lysozyme, 0.5 mg/ml RNase) and incubated overnight at 25° C. After overnight incubation, SDS and proteinase K were added to 6% and 0.5 mg/ml final concentration, respectively. The solution was incubated for 2 hours at 56° C. and submitted to 2 consecutive phenol extractions and one chloroform extraction. DNA was precipitated by the addition of half volume of 7.5 M ammonium acetate, 2 volumes of absolute ethanol and incubation at −20° C. during a couple of hours. The material was centrifuged during 15 minutes at 10,000 rpm and the pellet washed with 70% ethanol. Once dried, the pellet was resuspended in TE solution (10 mM Tris-HCl pH 7.4+1 mM EDTA)

The obtained genomic DNA was quantified by UV spectrophotometry at 260 nm wavelength and characterized by electrophoresis on a 0.8% agarose gel, using buffer TAE 1× (Tris-base 0.48%+acetic acid glacial 1.14%+EDTA 1 mM), and stained with a 0.5 µl/ml ethidium bromide solution.

A cloning strategy was designed in order to keep vector and insert in frame, allowing the correct translation of the protein fused with the fusion peptide.

The recombinant plasmid was sequenced and checked for the correct open reading frame of uveA gene and the nucleotide sequence of the fusion protein.

Figure 6:
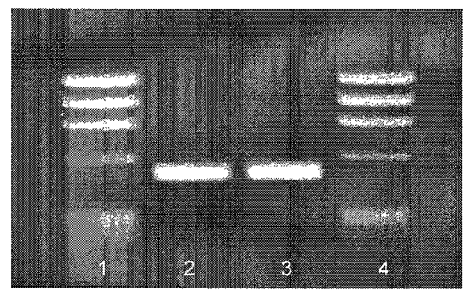
FIG. 6: PCR amplification of native UveA gen from *M. luteus*.

This 468 bp PCR fragment (FIG. 6) was purified, cloned into the pGEM-T-Easy cloning vector and subsequently subcloned into the expression vector.

3. Construction of the Prokaryotic Expression Vector

A. Amplification of uveA Gene by PCR

The uveA gene was amplified by PCR, and a Bgl II restriction enzyme recognition site was added at both ends of the amplified fragment. This complete procedure required two sets of reactions, using different oligonucleotides for the amplification of the first and second set of reactions.

The amplified PCR product was separated by electrophoresis in an 1.0% agarose gel using the φ174 RF DNA/HaeIII molecular weight marker. The obtained PCR product was excised, purified and quantified.

B. Cloning of uveA Gene

The uveA PCR fragment flanked by the restriction sites Bgl II, was ligated to the cloning vector pGEM-T-Easy. The product of ligase reaction was used to transform *E. coli* DH5α competent cells and the obtained recombinant colonies selected by color. Using the enzyme Bgl II, the insert was released from the "pGEM Bgl uveA" preparation. Once purified, the fragment was used to be ligated into a Bgl II restriction site from a the pEX vector. This cloning procedure allowed to leave in the 5' position (related to the uveA gene) a fragment whose sequence is:

```
ATG TGT GAT TTA CCT CAA ACT CAT TCT CTT GGT
TCT CGT CGT ACT CTG ATG CTG CTG GCA CAG ATG CGT
CGT ATT TCC CTG TTC AGC TGC CTG AAA GAC CGT CAC
GAC TTC GGC TTT CCG CAA GAA GAG TTC GGC AAC CAA
TTC CAG AAA GCT GAA ACT ATC CCA GTA CTG CAC GAA
ATG ATC CAA CAG ATC TT
``` which codes to the 65-long stabilizing amino acid peptide:

Met Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile Leu.

The resulting construct is the recombinant fusion enzyme, which is the fusion of the 65-long peptide sequence on the N-terminal regarding the uveA gene.

C. Induction of the Vector for the Expression

The pEX vector allows the utilization of thermo-sensitive repressors for the regulation of the expression, i.e., it regulates the gene expression by the lambda phage $P_L$ promoter. The strain ENV1 from *E. coli* contains the thermo-sensitive repressor which blocks the DNA transcription (the c1857/cro from lambda bacteriophage integrated into the bacterial chromosomal DNA). When the temperature rises to 42° C. the repressor is inactivated and the gene transcription starts.

ENV1 competent bacteria were transformed with the pEX vector containing the recombinant fusion enzyme fragment. The pEX-recombinant fusion enzyme allows the expression of huge amounts of recombinant fusion enzyme.

Since the repressor is thermo-sensitive, the transformed bacteria were grown always at 28° C., except during expression phase.

The expression assays were performed by inoculation of transformed bacteria into 2 ml LB broth+100 μg/ml ampicilin and grown overnight in a shaker. Using these overnight cultures, 50 ml LB broth supplemented with 100 μg/ml amp (dispensed into 250 ml Erlenmeyers) were inoculated and incubated under agitation until reaching and optical density (600 nm) of 0.4 (about 3 hours long). A culture sample was taken before inducing the expression of the recombinant protein, and then the temperature was rapidly raised to 42° C. to inactivate the repressor. These conditions were kept during 3 additional hours.

The expression of the recombinant fusion enzyme was analyzed by direct observation of polyacrylamide gel electrophoresis. For such purpose, the samples taken from the induced and non-induced ENV1 cultures, previously transformed with the pEX-recombinant fusion enzyme, were separated by 15% SDS-polyacrylamide gel electrophoresis (PAGE) and stained with Coomassie Blue. Every gel lane was loaded with a crude extract corresponding to approximately $1 \times 10^9$ bacteria. The bacterial crude extract corresponding to the induced ENV1 culture (pEX-recombinant fusion enzyme) presented a predominantly intense band with a relative molecular weight of about 26 kD, coincident with the theoretical weight for the recombinant fusion enzyme (FIG. 7).

Figure 8:
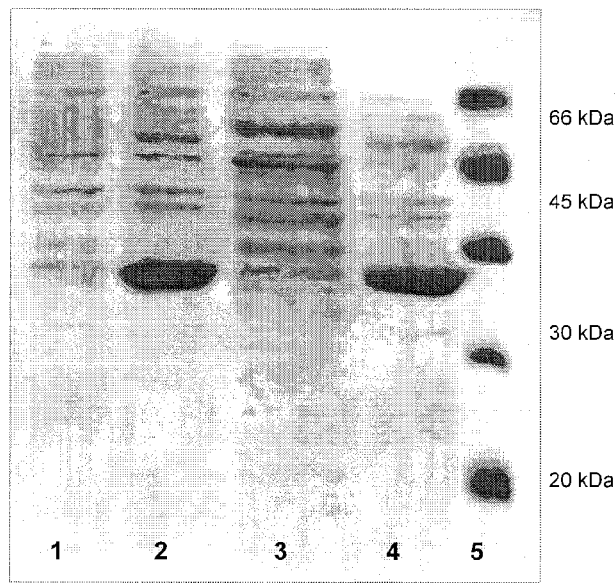
FIG. 8: Expression of recombinant fusion enzyme on soluble and insoluble fractions of ENV1 culture (pEX-"recombinant fusion enzyme").
Figure 9:
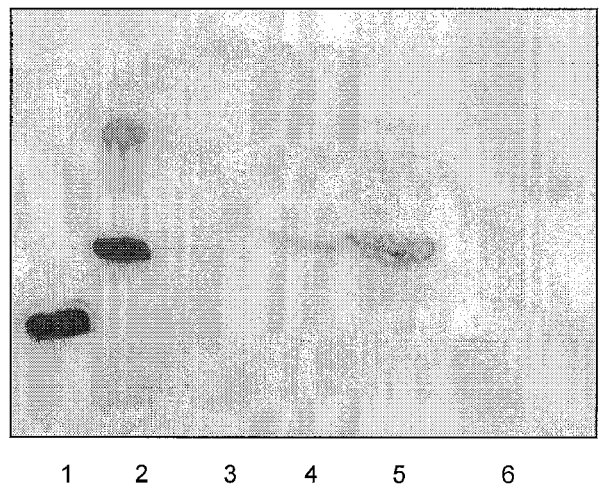
FIG. 9: Expression of recombinant fusion enzyme in an induced culture.

Usually, when heterologous proteins in *E. coli* reach high levels of expression, these proteins cannot remain as soluble forms into the cytoplasm, but they tend to form amorphous aggregates, not crystalline, insoluble and presented as intermediate protein-folding forms named inclusion bodies. To verify this hypothesis, assays on soluble and insoluble fractions of the ENV1 culture expressing the recombinant fusion enzyme were performed in a 15%-SDS polyacrylamide gel electrophoresis stained with Coomassie Blue. Every lane was loaded with a crude extract corresponding to approximately $1 \times 10^9$ bacteria (FIG. 8). The expression of recombinant fusion enzyme in induced cultures was also analyzed by the Western Blot technique probed with polyclonal antibodies against IFNα (FIG. 9), where the lanes 3, 4 and 5 from the gel were loaded with approximately 20 μg of total proteins, corresponding to $1 \times 10^9$ bacteria. It was found that the recombinant fusion enzyme (estimated molecular weight of 26 kD) was present into the insoluble fraction of inclusion bodies.

4. Obtainment of the Recombinant Fusion Enzyme

Fermentation

To work in a pilot production scale, a 8-liter capacity fermenter (Biostat C—Braun Biotech International) was used. This chosen equipment is sterilizable by a steam in place system and is equipped with controllers for pH and dissolved $O_2$.

The culture media used contained 160 g triptone, 80 g yeast extract, 20 g $K_2HPO_4$ and 20 g NaCl. The pH was set at 7.2. The fermenter was autoclaved in place during 30 minutes at 115° C. and 3.5 bars.

The inoculum ($OD_{600nm}$ 1.835) for the fermentation process was an overnight culture of ENV1 (pEX-recombinant fusion enzyme) grown in 600 ml LB broth at 28° C. and 250 rpm.

The fermenter media was inoculated with this grown culture plus 320 ml of a 50% (w/v) glucose solution, 40 ml of a 1 M $MgCl_2$ solution, 4 ml of a 100 μg/ml ampicilin solution and an antifoam agent (0.6% v/v).

The process was started under these parameters:

| | |
|---|---|
| Temperature: | 28° C. |
| $pO_2$: | 50% saturation |
| Agitation: | 300 rpm |
| Pressure: | 0.5 bar |

Figure 10:
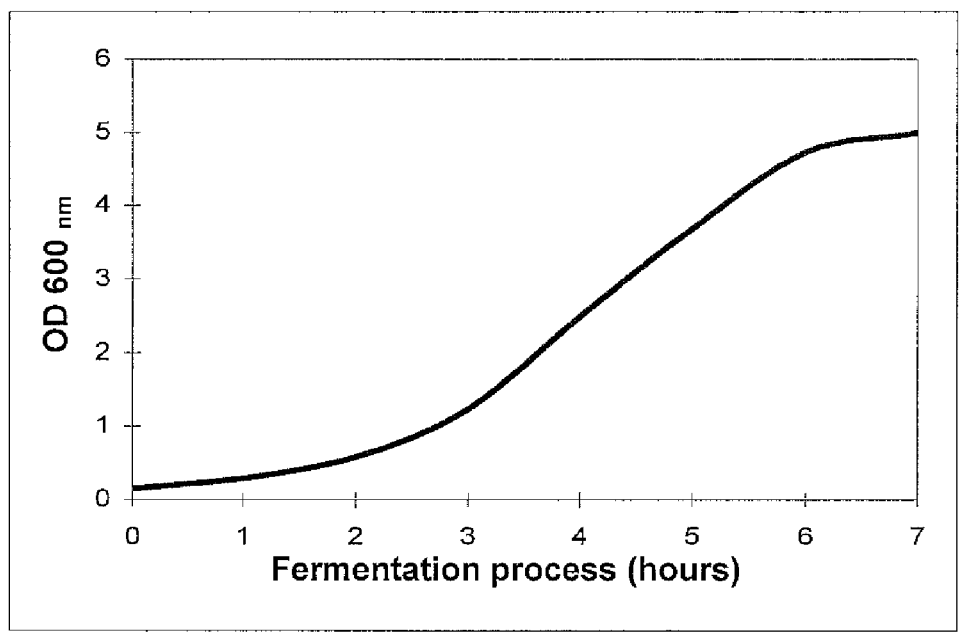
FIG. 10: Bacterial growth curve during fermentation.
Figure 11:
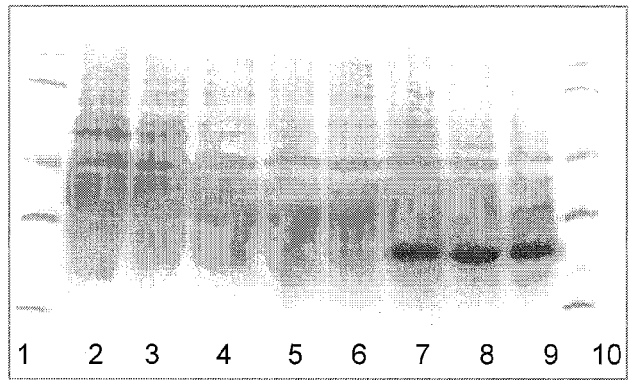
FIG. 11: Fifteen percent SDS-polyacrylamide gel electrophoresis stained with Coomassie Blue. Samples were harvested at one-hour intervals from fermentation.

The process was kept under these conditions during the first 4 hours. After this period of time the culture was induced by raising the temperature and the agitation to 42° C. and 500 rpm, respectively, during 3 hours. Samples were taken within one-hour intervals. The optical density was measured at 600 nm, observing that the samples fit into a range of 0.2 to 0.6 units for that wavelength (FIG. 10) and also observing the beginning of the induction phase at 42° C. during the $4^{th}$ hour of fermentation process. Additionally, hourly samples were taken and submitted to electrophoresis in a 15% SDS-Page stained with Coomassie Blue; every lane in the gel was loaded with approximately $1.0 \times 10^9$ bacteria, with presence of a band corresponding to the recombinant fusion enzyme (FIG. 11) being present on the last 3 lanes.

Once the fermentation process was concluded, the 8-liter culture was concentrated by tangential flow filtration through a 750 kDa membrane, to obtain a final volume of 600 ml. This concentrate was centrifuged during 10 minutes at 7,000 g. The supernatant was discarded. The precipitate was resuspended in 200 ml of a lysis solution (50 mM Tris-HCl, pH 8.0, 2 mM EDTA, 100 mM NaCl, 0.5 mg/ml lysozyme and 1 mM PMSF) and incubated during one hour at room temperature under low agitation. In order to reduce the media viscosity due cell disruption, the preparation was sonicated during 5 minutes at maximum potency, into an ice bath to avoid foam formation. Five hundred microliters of DNase were added to the preparation and incubated for one hour at room temperature. The sonication cycle into the ice bath was repeated and the material was centrifuged during 15 minutes at 12,000 rpm. The supernatant was discarded and the remaining material washed with distilled water, resuspending it several times with a syringe. The centrifugation and washing steps were repeated and the obtained material was fractionated and stored at −20° C. or alternatively used immediately.

Purification: Solubilization and Refolding

The proteins included as part of the inclusion bodies are characterized by a folding pattern depicting a high content of β-sheets, intermolecular bounds and intermediate foldings. These folding patterns are completely incompatible with enzymatic activity and require to be reversibly denatured and then refolded to its native active conformation, under oxidative conditions.

To purify the recombinant fusion enzyme, the inclusion bodies were resuspended and washed in Solution A (50 mM $K_2HPO_4$, pH 7.4, 150 mM NaCl and 1 mM EDTA) during 10 minutes and centrifuged at 6,000 g, 4° C., during 15 minutes. Once the supernatant was discarded, the precipitated material washed during 20 minutes with a Solution A containing 2 M urea, under low agitation at room temperature. The material was centrifuged at 6,000 rpm during 15 minutes at the same temperature. The precipitated material obtained in this last step washed during 20 minutes with Solution B (0.5% Triton X-100, 10 mM EDTA) under gentle stirring. The material was centrifuged at 10,000 rpm during 10 minutes, the supernatant was discarded and the pellet washed twice with Solution A. Urea was used as a chaotropic agent to solubilize the inclusion bodies, which were solubilized on water. The solubilization process was performed with a protein concentration close to 4.5 mg/ml.

Urea was added to reach a 8 M final concentration. The material was disrupted until the solution became translucent and afterwards a 100 mM glycine solution pH 10 was added, followed by a 100 mM NaCl and a 0.5% β-ME solution, respectively. The material was incubated during one hour at 4° C. under constant vortex stirring in order to complete the solubilization process. No protein precipitation was observed. The refolding operation was performed by means of a fast dilution of solubilized material into an oxidizing solution (1:30 fold dilution to obtain a 0.15 mg/ml final protein concentration) containing 25 mM Tris-HCl pH 8.0, 100 µM $CuCl_2$ (filtered through a 0.45 µm membrane), under constant agitation into an open reservoir, during 5 hours at approximately 20° C. The material was then dialyzed against a 50 mM Tris-HCl pH 8.0 solution during approximately 20 hours, with occasional solution exchange. The material was centrifuged at 10,000 rpm during 10 minutes to eliminate main multi-molecular aggregates.

Figure 12:
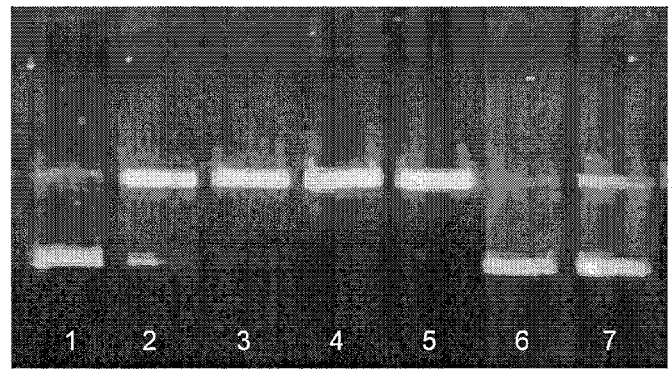
FIG. 12: UV-endonuclease specific activity assays.

The obtained folded fusion recombinant enzyme has shown to be enzymatically active. By means of a UV-specific endonuclease activity assay the solubilized preparation (FIG. 12) was confirmed to have an UV-specific endonuclease activity.

Figure 13:
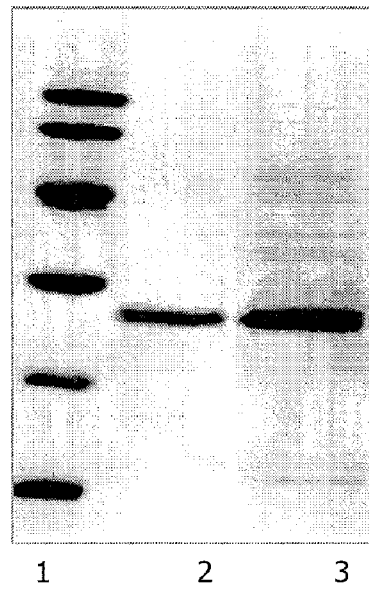
FIG. 13: Solubilization of inclusion bodies using 8M urea. Samples were run on a 15% SDS-polyacrylamide gel electrophoresis and stained with Coomassie Blue.
Figure 15:
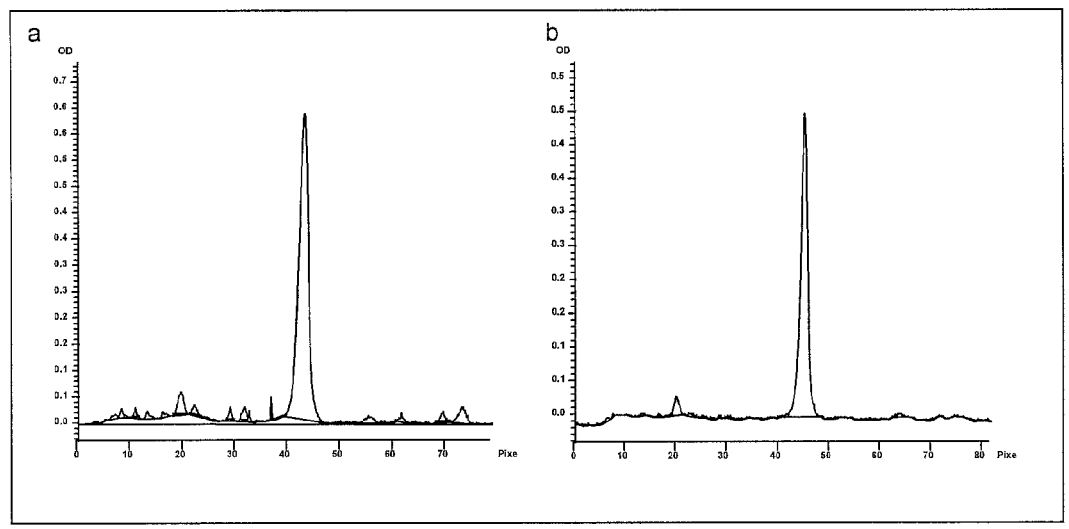
FIG. 15: Densitometry of protein profile from recombinant fusion enzyme preparation, run on 15% SDS polyacrylamide gel electrophoresis stained with Coomassie Blue.

The protein profile for every purification step was analyzed by electrophoresis in a 15% SDS-Page stained with Coomassie Blue. All obtained protein profiles was subjected to a densitometry analysis using the Image Quant software in order to evaluate purity for each sample (FIG. 13, FIG. 14 and FIG. 15). Additionally, the material was submitted to qualitative identity analysis by Western Blot. From these qualisemiquantitative analysis, considering the intensity of the band recognized by the antibody and its molecular weight, it was evident that the recombinant system pEX-recombinant fusion enzyme obtained expresses high levels of the recombinant fusion enzyme.

Purification Scheme for the recombinant fusion enzyme obtained from inclusion bodies:

| Step | Total Protein (g) | Recovery (%) | Purity (%) | Monomer (%) |
|---|---|---|---|---|
| bacterial pellet (520 g) | — | — | — | — |
| inclusion bodies (173 g) | 10.4 | — | 75 | — |
| First wash, A Solution | 8.63 | 83 | 89 | 85 |
| Wash, Urea 2M | 8.32 | 80 | 93 | 90 |
| Wash, B Solution (Triton X-100) | 7.9 | 76 | 98 | 94 |
| Second Wash, A Solution | 7.8 | 75 | 99 | 95 |
| Third Wash, A Solution | 7.8 | 75 | 99 | 96 |
| Solubilization, 8M Urea 100 mM glycine pH 10 5% β-ME 100 mM NaCl | | | | |
| Refolding 100 mM glycine pH 10 1 M L-α-arginine 100 mM NaCl 100 µM $CuCl_2$ | 1.03 | 10 | 99 | 98 |

Percentages for purity and recovery during the process. Inclusion bodies: expressed as wet weight. The recovery percentage was calculated from inclusion bodies preparation.

Oxidation and Refolding Conditions:

| Solubilization | refolding | Relaxed. total 200 ng of plasmid | Specific Activity |
|---|---|---|---|
| 8 M urea 100 mM glycine pH 10 5% β-ME 100 mM NaCl | 100 mM glycine pH 10 1 M L-α-Arginine 100 mM NaCl 100 µM $CuCl_2$ | 20 ng | 50,000 U/mg |

5. UV-Specific Endonuclease Activity Assay

The UV-specific endonuclease activity assay is based on the delay in electrophoretical migration produced by a UV-irradiated plasmid, after having one of its DNA strands nicked by the action of the recombinant fusion enzyme, and allowing the supercoiled structure of the closed circle become relaxed. Based on this, it is possible to distinguish the supercoiled plasmid (closed circle) from the plasmid having a cut in one of its strands (open circle).

A UV-specific endonuclease activity assay was performed for every preparation using different concentrations of the recombinant fusion enzyme in order to determine the minimum amount of proteic mass required to transform completely 200 ng of supercoiled (or closed circle) plasmid into relaxed (open circle) form.

One unit of enzymatic activity was arbitrarily defined as the mass of recombinant fusion enzyme required to relax 200 ng of irradiated pUC19. The several obtained preparations were analyzed comparatively according to the specific activity, which expresses the amount of units of enzymatic activity per mg of protein.

To perform the activity assay, the substrate was prepared as follows: pUC19 supercoiled DNA with a concentration of 25 ng/µl was irradiated with 100 J/m$^2$ using a 15 W UVC lamp.

The reaction containing 200 ng of irradiated pUC19 was incubated with the enzymatic fraction of the recombinant fusion enzyme to be studied. The reaction was performed in a buffer containing 25 mM NaHPO4 pH 7.0, 1 mM EDTA, 100 mM NaCl and 1 mM DTT, at 37° C. during one hour. For every tube containing irradiated plasmid, a second identical tube containing non-irradiated pUC19 plasmid was prepared to corroborate the UV specificity of the endonuclease activity. The reactions were separated by electrophoresis in 0.8% agarose gel, using buffer TAE 1×.

6. Comparative Stability Assay

The fraction containing enzymatic activity was adjusted to a concentration of 15 ng/µl with bovine serum albumin in order to correlate with the recombinant fusion enzyme solution, and lately divided in several tubes, half of them were stored at 4° C. and the remaining were stored at a temperature around 22° C. The same procedure was applied to the recombinant fusion enzyme solution.

Both native uveA and recombinant fusion enzyme preparations, stored at 4° C. and 22° C., were scanned for enzymatic activity, over the 2 years storage period. The percentage of relaxed irradiated plasmid was quantified by electrophoresis in agarose gel.

Figure 16:
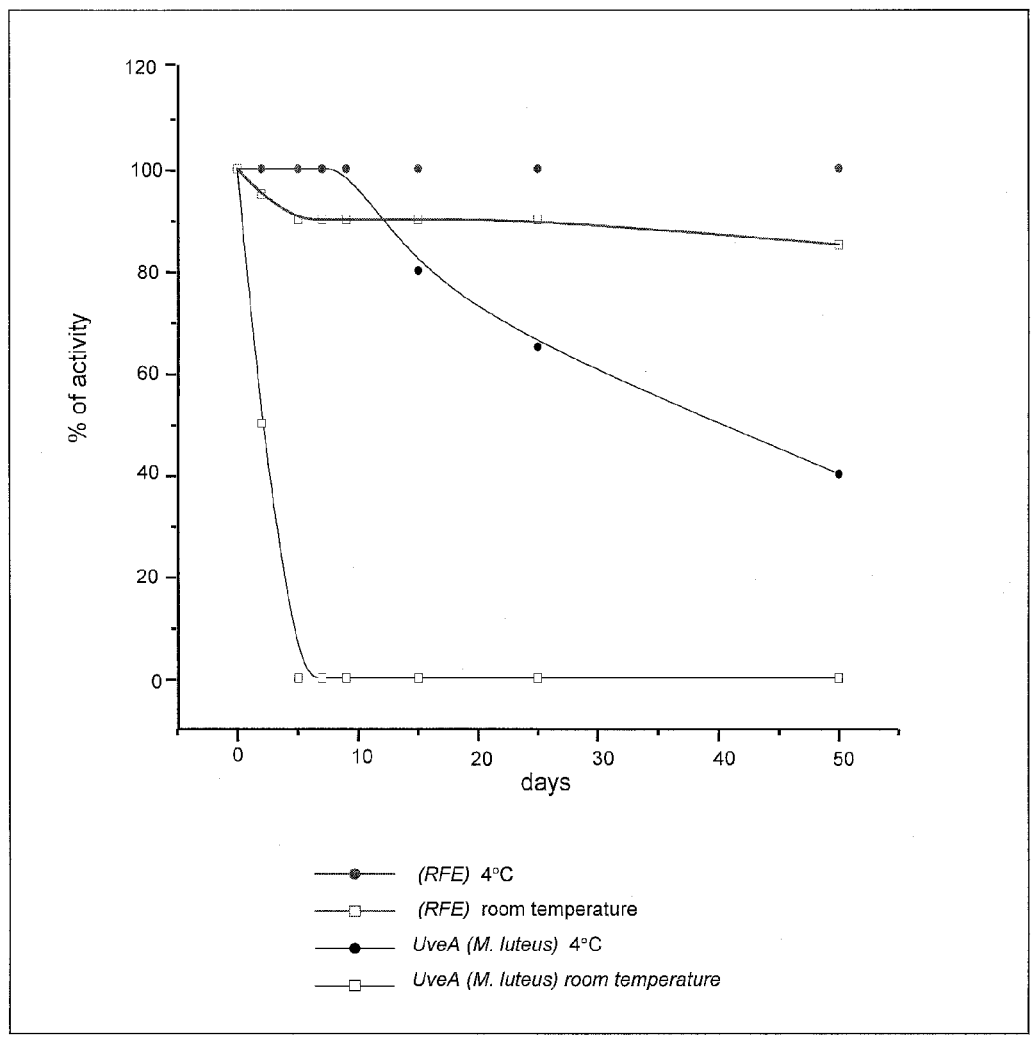
FIG. 16: Comparative stability between the fusion recombinant enzyme and the native UveA enzyme.

As observed in FIG. 16, the native uveA activity decreased over the first days of storage at room temperature. On the other hand, the recombinant fusion enzyme kept the percentage of activity closer to 100% until the end of the storage period. These values were kept between 80-90% at 4° C., for a period of 24 months.

The principles, the chosen approaches and the modus operandi of this invention have been described in the present document. However it is to be understood that the invention intended to be protected under this patent is not limited to the disclosed descriptive forms presented herein but to be considered as mere example. Amendments and alterations may be applied by the specialists in this field without changing the scope of this claim.

The afore-described recombinant fusion enzyme proved to be the most stable form both at 4° C. and room temperature, which facilitates its transport and formulation, and also is protective during exposure of XPC cells to UV radiation, known to be sensitive to UV radiation due genetic deficiencies on their repair mechanisms. Additionally, the expression system used for this recombinant enzyme is able to produce huge amounts of recombinant product.

The afore-described method includes the preparation and purification method for the recombinant fusion enzyme; as well as its utilization as part of a pharmaceutical formula intended to repair DNA lesions and/or cell abnormalities produced by UV light exposure and/or the prevention and prophylaxis of skin cancer.

BIBLIOGRAPHY

1. Friedberg E., Walter G and Siede. in DNA Repair and Mutagenesis, ASM Press, 1995, pages 634-646.
2. Guillermo Basilico, Carolina Alvarez Roger, Mauricio Seigelchifer and Nestor Kerner, UV-specific DNA repair recombinant fusion enzyme: a new stable pharmacologically active principle suitable for photoprotection. Journal of Dermatological Science, 2005, 39 (2), 81-88.
3. Boiteux S and Laval J, Repair of oxidized purines in DNA, chapter 3 in Base Excision Repair of DNA Damage, ed. Ian Hickson, 1997 Landes Bioscience.
4. Emmert S, Kobayashi N, Khan S and Kremer K, PNAS 97 (2000), 2151-2156.
5. Liu L., Nakatsuru Y and Gerson S., Base excision repair as a therapeutic target in colon cancer, Clinical Cancer Research 8, (2002), 2985-2991.
6. Morikawa K and Shirakawa M., Three-dimensional structure views of damaged-DNA recognition: T4 endonuclease V, *E. coli* Vsr protein and human nucleotide excision repair factor XPA, Mutation Research 460 (2000), 257-275.
7. Nominé Y., Ristriani T., Laurent C., Lefevre J. F., Weiss E., Travé G. (2001). Formation of soluble inclusion bodies by HPV E6 oncoprotein fused to maltose-binding protein. *Protein Expression and Purification* 23: 22-32.
8. Paul R., Bosch F., Schäfer K. P. (2001). Overexpression and purification of *Helicobacter pylori* flavodoxin and induction of a specific antiserum in rabitts. *Protein Expression and Purification* 22: 399-405.
9. Riazuddin S. (1980). Purification and properties of pyrimidine dimer specific endonucleases from *Micrococcus luteus*. Methods in Enzymology 65: 185-191.
10. Shiota S., Nakayama H. (1997). UV endonuclease of *Micrococcus luteus*, a cyclobutane pyrimidine dimer-DNA glycosylase/abasic lyase: cloning and characterization of the gene. *Proceedings National Academy of Science USA* 94: 593-598.
11. Tomilin N. and Zherebtsov S, An analysis of the repair processes in ultraviolet-irradiated *Micrococcus luteus* using purified ultraviolet-endonuclease, Biochimica et Biophysica Acta 698, (1982), 287-294.
12. Yarosh D., Klein J., O'Connor A., Hawk J., Rafal E., Wolf P. (2001). Effect of topically applied T4 endonuclease V in liposomes on skin cancer in xeroderma pigmentosum: a randomised study. *The Lancet* 357: 926-929.
13. Wood R., DNA Repair in Eukaryotes, Annu Rev Biochem 65, (1996), 135-167.

The invention claimed is:

1. A recombinant fusion enzyme having repair activity for DNA damaged by UV radiation, said enzyme comprises the amino acid sequence of SEQ. ID NO: 4, wherein said sequence is encoded by the nucleotide sequence of SEQ. ID NO: 1.

2. The recombinant fusion enzyme of claim 1, said enzyme further comprises a first DNA repairing enzyme encoded by the uveA gene isolated from *Micrococcus luteus*, bound to a second peptide originated from human interferon alpha 2.

3. The recombinant fusion enzyme of claim 1, wherein the second peptide comprises the amino acid sequence of SEQ ID NO: 3.

4. A UV radiation damaged DNA repairing composition, said composition comprising the recombinant fusion enzyme of claim 1.

5. The composition of claim 4, said enzyme further comprises the amino acid sequence of SEQ ID NO: 3.

6. The composition of claim 5, further comprising a peptide.

7. The composition of claim 6, further comprising in combination a second peptide, said second peptide being human interferon alpha 2.

8. A recombinant fusion enzyme having repair activity for DNA damage by UV radiation, said enzyme comprises the amino acid sequence of SEQ ID. NO: 4.

9. The recombinant fusion enzyme of claim 8, wherein said sequence is encoded by the nucleotide sequence of SEQ ID NO: 1.

* * * * *